United States Patent
Jia et al.

(10) Patent No.: US 10,584,093 B2
(45) Date of Patent: Mar. 10, 2020

(54) METHOD AND CATALYST FOR PREPARING ANILINE COMPOUNDS AND USE THEREOF

(71) Applicant: Seasons Biotechnology (Taizhou) Co., Ltd., Taizhou (CN)

(72) Inventors: Qiang Jia, Taizhou (CN); Chi Ma, Taizhou (CN); Tianhua Ma, Taizhou (CN); Zhengwei Yang, Taizhou (CN)

(73) Assignee: Seasons Biotechnology (Taizhou) Co., Ltd., Taizhou (CN)

( * ) Notice: Subject to any disclaimer, the term of this patent is extended or adjusted under 35 U.S.C. 154(b) by 0 days.

(21) Appl. No.: 16/142,369

(22) Filed: Sep. 26, 2018

(65) Prior Publication Data

US 2019/0100486 A1 Apr. 4, 2019

(51) Int. Cl.
| | |
|---|---|
| *C07C 209/36* | (2006.01) |
| *C07C 213/02* | (2006.01) |
| *B01J 23/28* | (2006.01) |
| *C07C 253/30* | (2006.01) |
| *C07D 295/135* | (2006.01) |
| *B01J 21/18* | (2006.01) |
| *C07C 319/20* | (2006.01) |

(52) U.S. Cl.
CPC .............. *C07C 209/36* (2013.01); *B01J 21/18* (2013.01); *B01J 23/28* (2013.01); *C07C 209/365* (2013.01); *C07C 213/02* (2013.01); *C07C 253/30* (2013.01); *C07C 319/20* (2013.01); *C07D 295/135* (2013.01)

(58) Field of Classification Search
None
See application file for complete search history.

(56) References Cited

U.S. PATENT DOCUMENTS 2,402,439 A * 6/1946 Owen .................. C07C 209/36
564/421

FOREIGN PATENT DOCUMENTS

CN 105669338 A 6/2016

OTHER PUBLICATIONS

Ferrari ("Influence of the active phase loading in carbon supported molybdenum-cobalt catalysts for hydrodeoxygenation reactions" Microporous and Mesoporous Materials, 2002, 56, p. 279-290) (Year: 2002).*
Huang ("N-doped graphitic carbon-improved Co-MoO3 catalysts on ordered mesoporous SBA-15 for chemoselective reduction of nitroarenes" Applied Catalysis A, General, 559, Apr. 22, 2018, p. 127-137) (Year: 2018).*
Zhang ("Transfer hydrogenation of nitroarenes with hydrazine at near-room temperature catalyzed by a MoO2 catalyst", 2016, vol. 18, p. 2435-2442, including Supporting Information p. S1-S12) (Year: 2016).*
Zhou ("Reduction of Nitrobenzene with Hydrazine Hydrate Catalyzed by Acid-Treated Activated Carbon" Chinese Journal of Catalysis, 2012, vol. 33, issue 9, p. 1463-1469) (Year: 2012).*
Academic Press Dictionary of Science and Technology definition for "activated carbon", downloaded from https://search.credoreference.com/content/entry/apdst/activated_carbon/0 on Jul. 16, 2019 (Year: 2019).*
Zhang et al., Green Chem., 18:2435-42 (2016).

* cited by examiner

*Primary Examiner* — Amy C Bonaparte

(74) *Attorney, Agent, or Firm* — RatnerPrestia

(57) ABSTRACT

The present invention provides a method for preparing aniline compounds, and also provides a kind of catalyst and use thereof. This method for synthesizing an aniline compound in the invention includes following steps: use molybdenum oxide and activated carbon as catalyst, hydrazine hydrate as reducing agent, then reduce aromatic nitro compounds to aniline compounds. This method is green and high efficiency, and easy to be applied in industry.

10 Claims, No Drawings

METHOD AND CATALYST FOR PREPARING ANILINE COMPOUNDS AND USE THEREOF

CROSS-REFERENCE TO RELATED APPLICATIONS

This claims priority to Chinese Application No. CN2017109105568, filed Sep. 29, 2017. The contents of which are incorporated herein by reference in their entireties for all purposes.

FIELD OF THE INVENTION

The present invention relates to synthetic method of aniline compounds. Specifically, it relates to a method for preparing aniline compounds by reducing aromatic nitro compounds. It also relates a kind of catalyst and its use in the synthesis of aniline compounds.

BACKGROUND OF THE INVENTION

Aniline compounds are an important class of chemical raw material. They are widely used in antioxidant, dye intermediates, imaging materials, pharmaceuticals and pesticide chemicals Aniline compounds are mainly prepared by reducing aromatic nitro compounds. At present, the methods of industrially reducing aromatic nitro compounds to produce aniline compounds mainly include metal reduction, alkali sulfide reduction, catalytic hydrogenation reduction, hydrazine hydrate reduction and electrochemical reduction. In these methods, the hydrazine hydrate reduction method is environmentally friendly and easy to operate, but the deficiency is that it needs a precious metal catalyst, a long time to react, and a large amount of non-environmentally friendly solvent. Patent Document CN105669338 and Document published in Green Chem. 2016, 18, 2435-2442 both reported a method of reducing a series of aromatic nitro compounds by using molybdenum oxide as metal catalyst and hydrazine hydrate as a reducing agent. Although the catalytic system provided by this method can catalyze the reduction of simple nitro-compounds such as nitrobenzene into aniline compounds, there are also obvious defects: one is that the catalyst molybdenum oxide need to be special prepared into $MoO_2$ nanoparticles, for example, need to be reduction prepared at high temperature of 350-600° C., and under hydrogen atmosphere. Or other strong conditions, such as hydration preparation for a long time at 160-250° C. autoclave; reduction with $N_2/H_2$ at 500° C. high temperature then treat with strong corrosive KF. The preparation conditions of $MoO_2$ nanoparticles are very demanding and very dangerous, which is difficult to obtain. Secondly, the amount of catalyst is large, the amount of charging molar ratio in nitrobenzene reduction is as high as 31%, and the charging mass ratio is 32%, which is far away from the requirement of the amount of catalyst. Third, the recovery and reuse of catalyst is not so good, and the best times of recycling do not exceed 3 times. All these existing defects greatly limit the practical application of this method in industrialization. The main reasons for these shortcomings are: On the one hand, self-made molybdenum oxide catalyst needs strict preparation, the preparation process is not easy to control, the prepared catalyst component is not certain, and the stable catalytic performance cannot be guaranteed. On the other hand, as the charging molar amount of catalyst is over 30%, it is not suitable to be used as catalyst. There are problems in the selection of catalyst and catalytic system. Therefore, it is necessary to develop a new method for green and efficient synthesis of aniline compounds which is easier to be applied in industrialization.

SUMMARY OF THE INVENTION

In view of the defects in the conventional methods, the objective of the present invention is to provide a method to prepare aniline compounds which is green and high efficiency, and easy to be applied in industry. At the same time, the present invention also provides a catalyst and its use in the synthesis of aniline compounds.

For the purpose of the invention, the technical solution adopted is as follows:

The first aspect of the invention provides a method for preparing aniline compounds which includes the following steps: use molybdenum oxide and activated carbon as catalyst, hydrazine hydrate as reducing agent, then reduce aromatic nitro compounds into aniline compounds.

Preparation for aniline compounds with the method in this invention and using molybdenum oxide and activated carbon as catalyst could reduce the charging amount of molybdenum oxide catalyst, catalyst is easy to be recycled, the catalyst can be directly recycled many times after simple filtering, and the times of recycling can reach to more than 10, which not only reduce the process cost, but also reduce the frequency of solid waste in the production. Wherein simple filtering can be, for example, filtering by means of pumping and nitrogen pressure filtration, and not limited to this, which achieving the purpose of filtering is enough. Based on this, in the preferred solutions of the invention, the method of the invention also includes the following steps: After reaction, filter reaction mixture; filter residue is used as the catalyst for recycling, which is used directly without further treatment. But in some specific examples, the filtrate is extracted to separate organic phase, which is further washed with water and then concentrated.

When using the method for preparing aniline compounds in the present invention, wherein preferred weight ratio of molybdenum oxide to activated carbon is from 1:1 to 1:10, more preferably, from 1:2 to 1:5. It is benefit for molybdenum oxide to be loaded on activated carbon uniformly under the optimum ratio, which increase the contact area between catalyst and aromatic nitro compound, so as to improve the catalytic effect of molybdenum oxide and finally increase the reaction rate.

The method for preparing aniline compounds in the present invention introduces activated carbon into reaction system, which greatly reduces the amount of molybdenum oxide in the catalyst. The molar ratio of molybdenum oxide to aromatic nitro compound mentioned in the preferred solution can be from 0.001:1 to 0.1:1, more preferably, from 0.01:1 to 0.03:1.

In the preferred solution in the invention, wherein the molybdenum oxide includes one or more compounds which have the formula: $MoO_x$ (x=2~3). When x=2 or 3, it represents $MoO_2$ or $MoO_3$. When x=2~3 (non-integer), it represents molybdenum oxide whose average valence is between +4 and +6 or $MoO_3$ partially reduced. Preferably, the molybdenum oxide is $MoO_2$, which can obtain better reaction rate and product yield.

The present invention provides a method for preparation aniline compounds, wherein the molybdenum oxide and activated carbon should be premixed before charged into the reaction system, or both charged into reaction system respectively without premixed. The molybdenum oxides and activated carbon used in the invention can be obtained from commercially available products; molybdenum oxides do not need nano-scale and conventional commercial grade reagents are enough. As an example, $MoO_2$ purchased from Sinopharm Chemical Reagent Co., Ltd., and activated carbon purchased from the Activated Carbon Branch of Hangzhou Wood Co., Ltd., the models are 772, 778, 779, 812, 862, 864, etc.

When using the method for preparing aniline compounds in the present invention, wherein the molar ratio of hydrazine hydrate to aromatic nitro compounds is preferably from 1.5:1 to 10:1, more preferably, from 2:1 to 4:1, where the molar ratio of hydrazine hydrate is calculated as pure hydrate.

The method for preparing aniline compounds in the present invention, wherein the preferred temperature of the reduction reaction is 25° C. to reflux. Method of the invention can be carried out under moderate condition, preferred reduction temperature can be controlled at 25-35° C. When preparing aniline compounds using method in the invention, it is no need to be protected with nitrogen, and could react in the environment connected with air. The reaction process is easy to control, operation is very simple and convenient, and the application suits a larger scope.

The method for preparing aniline compounds in the invention is not limited to reducing a certain aromatic nitro compound into corresponding aniline compound. As the preferred solution of the invention, the method of the invention reduces the aromatic nitro compounds as shown in the structural formula (I) to aniline compounds as shown in the structural formula (II):

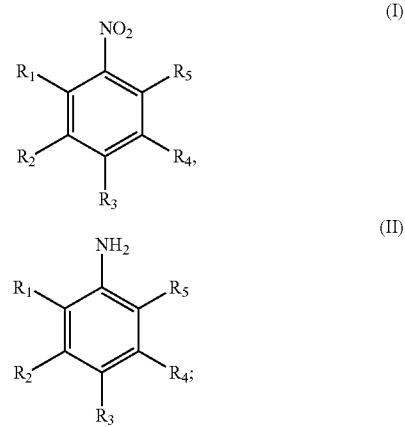

Wherein $R_1$-$R_5$ are the same or different from each other and each represents an optionally hydrogen atom, halogen atom, C1-C6 alkyl, phenyl or its substituents, benzyl or its substituents, $SR_6$, $OR_7$, $COOR_8$, $CONR_9R_{10}$ or CN; wherein $R_6$, $R_7$, $R_8$, $R_9$ and $R_{10}$ each represents an optionally hydrogen atom, C1-C6 alkyl, phenyl or its substituents, benzyl or its substituents, $R_9$ and $R_{10}$ are the same or different.

The substituents mentioned in the invention statement "phenyl or its substituents" represent mono-substituted or polysubstituted phenyl substituents, they can be the same or different. The preference of phenyl substituents are phenyl connected with C1-C6 alkyl, halogen atom, $SR_6$, $OR_7$, $COOR_8$, $CONR_9R_{10}$ or CN. When phenyl substituents are polysubstituted phenyl substituents, each substituent can independently select from those groups, wherein "polysubstituted" means two or more.

The substituents mentioned in the invention statement "benzyl or its substituents" represent mono-substituted or polysubstituted benzyl substituents, they can be the same or different. The preference of benzyl substituents are benzene on benzyl connected with C1-C6 alkyl, halogen atom, $SR_6$, $OR_7$, $COOR_8$, $CONR_9R_{10}$ or CN. When phenyl substituents are polysubstituted benzyl substituents, each substituent can independently select from those groups, wherein "polysubstituted" means two or more.

Wherein, $R_6$, $R_7$, $R_8$, $R_9$ and $R_{10}$ independently selected from hydrogen atom, C1-C6 alkyl, phenyl or its substituents, benzyl or its substituents, $R_9$ and $R_{10}$ are the same or different.

As an example, the aromatic nitro compounds in the present invention may be, for example, nitrobenzene, 4-nitrotoluene, 4-nitroanisole, 1-chloro-2-nitrobenzene, 1-fluoro-2-nitrobenzene, m-nitrochlorobenzene, m-nitrofluorobenzene, p-nitrochlorobenzene, p-fluoronitrobenzene, 2-(2,4-dimethylphenylsulfide)nitrobenzene, 3-(2,4-dimethylphenylsulfide)nitrobenzene, 4-(2,4-dimethylphenylsulfide) nitrobenzene, 1-cyano-4-nitrobenzene, 6-fluoro-2-nitrobenzoic acid, 2-nitro-4,5-bis (2-methoxyethoxy) benzonitrile or 2-nitro-4-methoxy-5-(3-morpholinylisopropyl) benzonitrile and the like.

The reduction reaction of the present invention is carried out in the presence of solvent which is protic solvent, preferably one or more than one selected from water, methanol, ethanol or isopropyl alcohol, more preferably ethanol.

The method for preparing aniline compounds in the invention, wherein hydrazine hydrate obtained from commercially available products is enough. The mass concentration of hydrazine hydrate aqueous solution can be selected from 40 to 80%, for example, 50% or 80%.

The second aspect of the present invention provides a catalyst, which includes molybdenum oxide and activated carbon. Preferably, the weight ratio of the molybdenum oxide to activated carbon is from 1:1 to 1:10, more preferably from 1:2 to 1:5.

The catalyst in the invention, wherein the molybdenum oxide includes one or more compounds which is have the formula: $MoO_x$ (x=2~3). When x=2 or 3, it represents $MoO_2$ or $MoO_3$. When x=2~3 (non-integer), it represents molybdenum oxide whose average valence is between +4 and +6 or $MoO_3$ partially reduced; more preferably, the molybdenum oxide is $MoO_2$.

The catalyst in the invention, wherein the molybdenum oxide and activated carbon can be mixed together for storage or stored separately. When molybdenum oxide and activated carbon mixed together for storage, they could be charged into the reaction system in the form of mixture. Or when they stored separately, they can be charged into reaction system respectively.

The third aspect of the invention also provides the use of catalyst described above, which can be used to catalyze the reduction of aromatic nitro compounds into aniline compounds. preferably, the catalyst is used to catalyze the reduction of aromatic nitro compounds into aniline compounds in the reaction system with hydrazine hydrate as the reducing agent. The catalyst molybdenum oxide and activated carbon can be premixed and then charged into the reaction system, or respectively charged into the reaction system.

Furthermore, in a preferred embodiment, after the reduction reaction is completed, the reaction mixture is filtered, and the filter residue is recovered and reused as a catalyst for recycling. The recovered catalyst can be recycled for more than 10 times while still maintaining high catalytic activity, and only simple filtration is required for recovery. The technical solution provided by the invention has the following beneficial effects:
(1) Adding small amount of activated carbon into the reduction system can greatly reduce the amount of catalyst molybdenum oxide. Moreover, the catalysts are easily recycled, and can be recycled several times directly through simple filtration, which will not only reduce the process cost, but also reduce the generation frequency of solid waste generation and the possibility of a large amount of metal ions residue remaining in the product. Compared with the prior art, for example, the conventional catalyst $FeCl_3$ is filtered directly after reaction is completed, the iron ions are still not completely removed. This is because $FeCl_3$ is ionized to form iron ions in aqueous solution, resulting in iron ions still exist in the solution, which increase the possibility of iron ion residue. In addition, for some heavy metal catalysts, such as platinum, palladium, etc., their residue detection requirements are higher. But for the catalyst molybdenum oxides (such as $MoO_2$) in the present invention, the oxidation state itself will not ionize even in aqueous solutions. Therefore, the metal molybdenum can be removed directly through filtration, thus reducing the possibility of residual molybdenum in solution.
(2) In the reaction system of the invention, both catalysts $MoO_2$ and activated carbon are common commercial commodities, which are cheap and easy to obtain. The most important is that commodity grade catalysts can be used, the commercial grade catalyst has a fixed composition and quality assurance, and the catalytic performance is stable. The purchased catalyst can be used directly without the need for rigorous pre-preparation. $MoO_2$ is not required to be nanoscale.
(3) The method for preparing aniline compounds in the invention also has the characteristics of wider application surface, more mild reaction conditions, easier and convenient operation. Without $N_2$ protection, the reaction can be conducted in environment with air. The reaction process is easy to control and complete, and the product has high purity and yield.

EXAMPLES

In order to better understand the technical solution of the invention, the content of the invention is further expounded with the examples below, but the content of the invention is not limited to the following examples only.

Both the examples and comparative examples involve "%", if not specifically stated, refer to quality percentages.

The following describes test instruments and part of experimental materials used in examples and comparative examples:

Materials, reagents and solvents: purchased commercially. Reagents such as hydrazine hydrate solution with quality concentration of 50% and 80%, and molybdenum dioxide, were purchased from Sinopharm Chemical Reagent Co., Ltd., and activated carbon was purchased from the Activated Carbon Branch of Hangzhou Wood Co., Ltd. All the solvents used were domestic analytical pure reagent without any treatment before used, and purchased from Sinopharm Chemical Reagent Co., Ltd.

High performance liquid chromatography: Agilent 1206.

Nuclear Magnetic Resonance Spectrometer: Bruker DRX-400FT (Germany), $^1$HNMR is detected in $CDCl_3$, DMSO-$d_6$ and $D_2O$, and the chemical shift was measured using tetramethylsilane (TMS) as the reference, unit ppm.

Example 1

Preparation of Aniline 1.58 g (10 mmol) of nitrobenzene, 25.6 mg (0.2 mmol) of $MoO_2$, 76.8 mg of activated carbon and 30 mL of ethyl alcohol were added into a 50 mL flask. Then 1.2 g (20 mmol) of hydrazine hydrate (80%) was added dropwise at room temperature and reacted at room temperature for 2 hours until TLC analysis showed the raw materials were reacted completely and then filtered, concentrated filtrate, extracted with 20 mL of ethyl acetate and 10 mL of water, the obtained organic phase was washed and concentrated, finally, get 1.22 g of light brown liquid, the molar yield was 100%, HPLC purity was 99.8%.

$^1$HNMR data: $^1$HNMR (400 MHz, $CDCl_3$) δ: 7.10-7.14 (m, 2H), 6.78-6.73 (m, 3H).

Example 2

Preparation of 4-methylaniline 1.37 g (10 mmol) of 4-methylnitrobenzene, 25.6 mg (0.2 mmol) of $MoO_2$, 76.8 mg of activated carbon and 30 mL of ethyl alcohol were added into a 50 mL flask. Then 1.2 g (20 mmol) of hydrazine hydrate (80%) was added dropwise at room temperature and reacted at room temperature for 2 hours until TLC analysis showed the raw materials were reacted completely and then filtered, concentrated filtrate, extracted with 20 mL of ethyl acetate and 10 mL of water, the obtained organic phase was washed and concentrated, finally, get 1.05 g of colorless solid, the molar yield was 98%, HPLC purity was 99.8%.

$^1$HNMR data: $^1$HNMR (400 MHz, $CDCl_3$) δ: 7.13-7.17 (m, 2H), 6.74-6.69 (m, 2H), 2.3 (s, 3H).

Example 3

Preparation of p-Methoxylaniline 1.53 g (10 mmol) of 4-nitroanisole, 25.6 mg (0.2 mmol) of $MoO_2$, 76.8 mg of activated carbon and 30 mL of ethyl alcohol were added into a 50 mL flask. Then 1.2 g (20 mmol) of hydrazine hydrate (80%) was added dropwise at room temperature and reacted at room temperature for 1.5 hours until TLC analysis showed the raw materials were reacted completely and then filtered, concentrated filtrate, extracted with 20 mL of ethyl acetate and 10 mL of water, the obtained organic phase was washed and concentrated, finally, get 1.2 g of colorless solid, the molar yield was 97.6%, HPLC purity was 99.6%.

$^1$HNMR data: $^1$HNMR (400 MHz, $CDCl_3$) δ: 7.11-7.14 (m, 2H), 6.75-6.71 (m, 2H), 3.65 (s, 3H).

Example 4

Preparation of o-Chloroaniline 1.58 g (10 mmol) of o-chloronitrobenzene, 25.6 mg (0.2 mmol) of $MoO_2$, 76.8 mg of activated carbon and 30 mL of ethyl alcohol were added into a 50 mL flask. Then 1.2 g (20 mmol) of hydrazine hydrate (80%) was added dropwise at room temperature and reacted at room temperature for 3 hours until TLC analysis showed the raw materials were reacted completely and then filtered, concentrated filtrate, extracted with 20 mL of ethyl acetate and 10 mL of water, the obtained organic phase was washed and concentrated, finally, get 1.22 g of light brown liquid, the molar yield was 95.3%, HPLC purity was 99.7%.

$^1$HNMR data: $^1$HNMR (400 MHz, CDCl$_3$) δ: 7.31-7.34 (m, 1H), 7.13-7.16 (m, 1H), 6.83-6.86 (m, 1H), 6.71-6.73 (m, 1H), 5.28 (s, 2H).

Example 5

Preparation of o-Fluoroaniline 1.41 g (10 mmol) of o-fluoronitrobenzene, 25.6 mg (0.2 mmol) of MoO$_2$, 76.8 mg of activated carbon and 30 mL of ethyl alcohol were added into a 50 mL flask. Then 1.92 g (20 mmol) of hydrazine hydrate (50%) was added dropwise at room temperature and reacted at room temperature for 4.5 hours until TLC analysis showed the raw materials were reacted completely and then filtered, concentrated filtrate, extracted with 20 mL of ethyl acetate and 10 mL of water, the obtained organic phase was washed and concentrated, finally, get 1.22 g of light brown liquid, the molar yield was 94.6%, HPLC purity was 99%.

$^1$HNMR data: $^1$HNMR (400 MHz, CDCl$_3$) δ: 7.30-7.33 (m, 1H), 7.13-7.16 (m, 1H), 6.82-6.85 (m, 1H), 6.75-6.78 (m, 1H), 5.29 (s, 2H).

Example 6

Preparation of m-Chloroaniline 1.58 g (10 mmol) of m-chloronitrobenzene, 25.6 mg (0.2 mmol) of MoO$_2$, 76.8 mg of activated carbon and 30 mL of ethyl alcohol were added into a 50 mL flask. Then 1.25 g (20 mmol) of hydrazine hydrate (80%) was added dropwise at room temperature and reacted at room temperature for 5 hours until TLC analysis showed the raw materials were reacted completely and then filtered, concentrated filtrate, extracted with 20 mL of ethyl acetate and 10 mL of water, the obtained organic phase was washed and concentrated, finally, get 1.21 g of light brown liquid, the molar yield was 94.5%, HPLC purity was 98.7%.

$^1$HNMR data: $^1$HNMR (400 MHz, CDCl$_3$) δ: 7.15-7.18 (m, 1H), 7.09-7.13 (m, 1H), 6.83-6.86 (m, 1H), 6.64-6.67 (m, 1H), 5.34 (s, 2H).

Example 7

Preparation of m-Fluoroaniline 1.41 g (10 mmol) of m-nitrofluorobenzene, 25.6 mg (0.2 mmol) of MoO$_2$, 76.8 mg of activated carbon and 30 mL of ethyl alcohol were added into a 50 ml flask. Then 1.92 g (20 mmol) of hydrazine hydrate (50%) was added dropwise at room temperature and reacted at room temperature for 4.5 hours until TLC analysis showed the raw materials were reacted completely and then filtered, concentrated filtrate, extracted with 20 mL of ethyl acetate and 10 mL of water, the obtained organic phase was washed and concentrated, finally, get 1.05 g of light yellow liquid, the molar yield was 94.6%, HPLC purity was 98.9%.

$^1$HNMR data: $^1$HNMR (400 MHz, CDCl$_3$) δ: 7.10-7.13 (m, 1H), 7.93-7.96 (m, 1H), 6.65-6.68 (m, 1H), 6.54-6.57 (m, 1H), 5.30 (s, 2H).

Example 8

Preparation of p-Chloroaniline 1.58 g (10 mmol) of p-chloronitrobenzene, 25.6 mg (0.2 mmol) of MoO$_2$, 76.8 mg of activated carbon and 30 mL of ethyl alcohol were added into a 50 mL flask. Then 1.2 g (20 mmol) of hydrazine hydrate (80%) was added dropwise at room temperature and reacted at room temperature for 5 hours until TLC analysis showed the raw materials were reacted completely and then filtered, concentrated filtrate, extracted with 20 mL of ethyl acetate and 10 mL of water, the obtained organic phase was washed and concentrated, finally, get 1.24 g of light yellow crystals, the molar yield was 96.9%, HPLC purity was 99.5%.

$^1$HNMR data: $^1$HNMR (400 MHz, CDCl$_3$) δ: 7.14-7.17 (m, 2H), 6.61-6.58 (m, 2H), 5.49 (s, 2H).

Example 9

Preparation of p-Fluoroaniline 1.41 g (10 mmol) of p-fluoronitrobenzene, 25.6 mg (0.2 mmol) of MoO$_2$, 76.8 mg of activated carbon and 30 mL of ethyl alcohol were added into a 50 ml flask. Then 1.25 g (20 mmol) of hydrazine hydrate (80%) was added dropwise at room temperature and reacted at room temperature for 4.5 hours until TLC analysis showed the raw materials were reacted completely and then filtered, concentrated filtrate, extracted with 20 mL of ethyl acetate and 10 mL of water, the obtained organic phase was washed and concentrated, finally, get 1.08 g of light yellow liquid, the molar yield was 97.3%, HPLC purity was 99.4%.

$^1$HNMR data: $^1$HNMR (400 MHz, CDCl$_3$) δ: 7.04-7.01 (m, 2H), 6.71-6.68 (m, 2H), 5.45 (s, 2H).

Example 10

Preparation of 2-(2,4-dimethylphenylthio)benzenamine 2.00 g (7.70 mmol) of 2-(2,4-dimethyl phenyl sulfide) nitrobenzene, 0.01 g (0.077 mmol) of MoO$_2$, 0.05 g of activated carbon and 30 mL of ethyl alcohol were added into a 50 mL flask. Then 0.92 g (15.0 mmol) of hydrazine hydrate (80%) was added dropwise at room temperature and reacted at room temperature for 6 hours until TLC analysis showed the raw materials were reacted completely and then filtered, concentrated filtrate, extracted with 20 mL of ethyl acetate and 10 mL of water, the obtained organic phase was washed and concentrated, finally, get 1.64 g of white solid, the molar yield was 93%, HPLC purity was 99.5%.

$^1$HNMR data: $^1$HNMR (400 MHz, CDCl$_3$) δ: 7.15-7.20 (m, 2H), 7.02 (s, 6.81-6.85 (m, 2H), 6.58-6.65 (m, 2H), 5.28 (s, 2H), 2.31 (s, 3H), 2.20 (s, 3H).

Example 11

Preparation of 3-(2,4-dimethylphenylthio)benzenamine 2.00 g (7.70 mmol) of 3-(2,4-dimethyl phenyl sulfide) nitrobenzene, 0.01 g (0.077 mmol) of MoO$_2$, 0.05 g of activated carbon and 20 mL of ethyl alcohol were added into a 50 mL flask. Then 1.47 g (15.0 mmol) of hydrazine hydrate (50%) was added dropwise at room temperature and reacted at room temperature for 5.5 hours until TLC analysis showed the raw materials were reacted completely and then filtered, concentrated filtrate, extracted with 20 mL of ethyl acetate and 10 mL of water, the obtained organic phase was washed and concentrated, finally, get 1.6 g of white solid, the molar yield was 90.4%, HPLC purity was 99.1%.

¹HNMR data: ¹HNMR (400 MHz, DMSO-$d_6$) δ: 7.35-7.38 (m, 1H), 7.17-7.24 (m, 2H), 7.09-7.15 (m, 1H), 7.04 (s, 1H), 6.92-6.98 (m, 2H), 6.58-6.65 (m, 1H), 5.20 (s, 2H), 2.30 (s, 3H), 2.21 (s, 3H).

Example 12

Preparation of 4-(2,4-dimethylphenyithio)benzenamine 2.00 g (7.70 mmol) of 4-(2,4-dimethyl phenyl sulfide) nitrobenzene, 0.01 g (0.077 mmol) of $MoO_2$, 0.05 g of activated carbon and 20 mL of ethyl alcohol were added into a 50 mL flask. Then 1.47 g (15.0 mmol) of hydrazine hydrate (50%) was added dropwise at room temperature and reacted at room temperature for 6.5 hours until TLC analysis showed the raw materials were reacted completely and then filtered, concentrated filtrate, extracted with 20 mL of ethyl acetate and 10 mL of water, the obtained organic phase was washed and concentrated, finally, get 1.67 g of white solid, the molar yield was 94.4%, HPLC purity was 99.3%.

¹HNMR data: ¹HNMR (400 MHz, DMSO-$d_6$) δ: 7.18-7.23 (m, 1H), 7.02 (s, 1H), 6.80-6.87 (m, 3H), 6.60-6.66 (m, 2H), 5.28 (s, 2H), 2.31 (s, 3H), 2.20 (s, 3H).

Example 13

Preparation of 4-aminobenzonitrile 1.48 g (10 mmol) of 1-cyano-4-nitrobenzene, 25.6 mg (0.2 mmol) of $MoO_2$, 76.8 mg of activated carbon and 20 mL of ethyl alcohol were added into a 50 mL flask. Then 1.25 g (20 mmol) of hydrazine hydrate (80%) was added dropwise at room temperature and reacted at room temperature for 5 hours until TLC analysis showed the raw materials were reacted completely and then filtered, concentrated filtrate, extracted with 20 mL of ethyl acetate and 10 mL of water, the obtained organic phase was washed and concentrated, finally, get 1.1 g of solid, the molar yield was 93%, HPLC purity was 99%.

¹HNMR data: ¹HNMR (400 MHz, $CDCl_3$) δ: 7.23-7.27 (m, 2H), 6.81-6.87 (m, 2H), 5.63 (s, 2H).

Example 14

Preparation of 2-amino-6-fluorobenzoic acid 1.85 g (10 mmol) of 6-fluoro-2-nitrobenzoic acid, 25.6 mg (0.2 mmol) of $MoO_2$, 76.8 mg of activated carbon and 30 mL of ethyl alcohol were added into a 50 mL flask. Then 1.25 g (20 mmol) of hydrazine hydrate (80%) was added dropwise at room temperature and reacted at room temperature for 7 hours until TLC analysis showed the raw materials were reacted completely and then filtered, concentrated filtrate, extracted with 20 mL of ethyl acetate and 10 mL of water, the obtained organic phase was washed and concentrated, finally, get 1.5 g of light yellow solid, the molar yield was 96.8%, HPLC purity was 99.6%.

¹HNMR data: ¹HNMR (400 MHz, $D_2O$) δ: 7.45-7.40 (m, 1H), 6.86-6.95 (m, 2H).

Example 15

Preparation of 2-Amino-4,5-bis(2-methoxyethoxy)benzonitrile 2.96 g (10 mmol) of 2-nitro-4,5-bis (2-methoxyethoxy) benzonitrile, 38.4 mg (0.3 mmol) of $MoO_2$, 0.12 g of activated carbon and 30 mL of ethyl alcohol were added into a 50 mL flask. Then 1.88 g (30 mmol) of hydrazine hydrate (80%) was added dropwise at room temperature and reacted at room temperature for 7 hours until TLC analysis showed the raw materials were reacted completely and then filtered, concentrated filtrate, extracted with 20 mL of ethyl acetate and 10 mL of water, the obtained organic phase was washed and concentrated to near dry, slurryed with petroleum ether, finally, get 2.4 g of light yellow solid, the molar yield was 90.2%, HPLC purity was 99%.

¹HNMR data: ¹HNMR (400 MHz, $CDCl_3$) δ: 7.41 (s, 1H), 7.04 (s, 1H), 3.61-3.66 (m, 4H), 2.47-2.55 (m, 4H), 3.24 (s, 3H), 3.21 (s, 3H).

Example 16

Preparation of 2-amino-4-methoxy-5-(3-morpholinylisopropyl)benzonitrile 3.2 g (10 mmol) of 2-nitro-4-methoxy-5-(3-morpholinylisopropyl) benzonitrile, 38.4 mg (0.3 mmol) of $MoO_2$, 0.12 g of activated carbon and 30 mL of ethyl alcohol were added into a 50 ml flask. Then 1.88 g (30 mmol) of hydrazine hydrate (80%) was added dropwise at room temperature and reacted at room temperature for 7 hours until TLC analysis showed the raw materials were reacted completely and then filtered, concentrated filtrate, extracted with 20 mL of ethyl acetate and 10 mL of water, the obtained organic phase was washed and concentrated to near dry, slurryed with petroleum ether, finally, get 2.65 g of light yellow solid, the molar yield was 91%, HPLC purity was 99.3%.

¹HNMR data: ¹HNMR (400 MHz, $CDCl_3$) δ: 7.45 (s, 1H), 7.02 (s, 1H), 4.81-4.85 (m, 2H), 3.58-3.65 (m, 4H), 3.28 (s, 3H), 2.41-2.48 (m, 2H), 2.31-3.38 (m, 2H), 1.87-1.91 (m, 2H).

Example 17

Filter the reaction mixture and get filter residue from example 8 as catalyst. Experiment is carried out using recovered catalyst without any treatment, and the process which used the 10th catalysts is as below:

1.58 g (10 mmol) of p-chloronitrobenzene, $MoO_2$ and activated carbon (recovered from $9^{th}$ process) and 30 mL of ethyl alcohol were added into a 50 ml flask. Then 1.2 g (20 mmol) of hydrazine hydrate (80%) was added dropwise at room temperature and reacted at room temperature for 5 hours until TLC analysis showed the raw materials were reacted completely and then filtered, concentrated filtrate, extracted with 20 mL of ethyl acetate and 10 mL of water, the obtained organic phase was washed and concentrated, finally, get 1.24 g of light yellow crystals, the molar yield was 96.9%, HPLC purity was 99%.

Example 18

Filter the reaction mixture and get filter residue from example 10 as catalyst. Experiment is carried out using recovered catalyst without any treatment, and the process which used the 10th catalysts is as below:

2.00 g (7.70 mmol) of 2-(2,4-dimethyl phenyl sulfide) nitrobenzene, MoO$_2$ and activated carbon (recovered from 9$^{th}$ process) and 30 mL of ethyl alcohol were added into a 50 ml flask. Then 0.92 g (15.0 mmol) of hydrazine hydrate (80%) was added dropwise at room temperature and reacted at room temperature for 6 hours until TLC analysis showed the raw materials were reacted completely and then filtered, concentrated filtrate, extracted with 20 mL of ethyl acetate and 10 mL of water, the obtained organic phase was washed and concentrated, finally, get 1.64 g of white solid, the molar yield was 93%, HPLC purity was 99.4%.

Comparative Example 1

Compare with Example 1, experiment is carried out to prepare aniline without activated carbon, and the process is as below:

1.58 g (10 mmol) of nitrobenzene, 25.6 mg (0.2 mmol) of MoO$_2$ and 30 mL of ethyl alcohol were added into a 50 ml flask. Then 1.2 g (20 mmol) of hydrazine hydrate (80%) was added dropwise at room temperature and reacted at room temperature. TLC analysis showed almost no products were produced, HPLC showed raw material nitrobenzene was left 99%, and aniline was only 0.8%.

Comparative Example 2

Compare with Example 10, experiment is carried out to prepare 2-(2,4-dimethylphenylthio) benzenamine without activated carbon, and the process is as below:

2.00 g (7.70 mmol) of 2-(2,4-dimethyl phenyl sulfide) nitrobenzene, 0.01 g (0.077 mmol) of MoO$_2$ and 30 mL of ethyl alcohol were added into a 50 ml flask. Then 0.92 g (15.0 mmol) of hydrazine hydrate (80%) was added dropwise at room temperature and reacted at room temperature for 6 hours. TLC analysis showed almost no products were produced, HPLC showed raw material was left 99.3%, and product was only 0.3%.

Comparative Example 3

Compare with Example 10, experiment is carried out to prepare 2-(2,4-dimethylphenylthio) benzenamine without MoO$_2$, and the process is as below:

2.00 g (7.70 mmol) of 2-(2,4-dimethyl phenyl sulfide) nitrobenzene, 0.05 g activated carbon and 30 mL of ethyl alcohol were added into a 50 ml flask. Then 0.92 g (15.0 mmol) of hydrazine hydrate (80%) was added dropwise at room temperature and reacted at room temperature for 6 hours. TLC analysis showed almost no products were produced, HPLC showed raw material was left 99.3%, and product was only 0.3%.

Example 19

Compare with Example 10, experiment is carried out to prepare 2-(2,4-dimethylphenylthio) benzenamine with MoO$_3$, and the process is as below:

2.00 g (7.70 mmol) of 2-(2,4-dimethyl phenyl sulfide) nitrobenzene, 11.1 mg (0.077 mmol) of MoO$_3$, 0.05 g of activated carbon and 30 mL of ethyl alcohol were added into a 50 ml flask. Then 0.92 g (15.0 mmol) of hydrazine hydrate (80%) was added dropwise at room temperature and reacted at room temperature for 6 hours, TLC analysis showed there was still raw material left, then reacted at room temperature for another 6 hours until TLC analysis showed the raw materials were left less, filtered and concentrated filtrate, extracted with 20 mL of ethyl acetate and 10 mL of water, the obtained organic phase was washed and concentrated, slurryed with 10 mL of n-heptane for 1 hour, finally, get 1.42 g of white solid, the molar yield was 80.5%, HPLC purity was 98.5%.

$^1$HNMR data: $^1$HNMR (400 MHz, DMSO-d$_6$) δ: 7.15-7.20 (m, 2H), 7.02 (s, 1H), 6.81-6.85 (m, 2H), 6.58-6.65 (m, 2H), 5.28 (s, 2H), 2.31 (s, 3H), 2.20 (s, 3H).

Technicians in this field may understand and under the instruction of this invention, some modifications or adjustments can be made to the invention. Such modifications or adjustments should also be within the scope of the claims of the invention

The invention claimed is:

1. A method for preparing aniline compounds, comprising reacting aromatic nitro compounds with hydrazine hydrate in the presence of molybdenum oxide and activated carbon at a molar ratio of the molybdenum oxide to the aromatic nitro compounds from 0.005:1 to 0.05:1 to reduce the aromatic nitro compounds into aniline compounds, wherein the weight ratio of the molybdenum oxide to the activated carbon is from 1:2 to 1:8, whereby a reaction mixture comprising the aniline compounds is obtained.

2. The method according to claim 1, wherein the molybdenum oxide comprises one or more compounds having the formula MoO$_x$, wherein x is a number between 2 and 3, inclusive wherein when x=2 or 3, the molybdenum oxide is MoO$_2$ or MoO$_3$, and respectively, when x is a non-integer between 2 and 3, the molybdenum oxide has an average valence between +4 and +6.

3. The method according to claim 1, wherein the molybdenum oxide and the activated carbon are premixed before the reaction.

4. The method according to claim 1, wherein the molar ratio of the hydrazine hydrate to the aromatic nitro compounds is from 2:1 to 8:1.

5. The method according to claim 1, wherein the temperature of the reaction is 25° C. to reflux.

6. The method according to claim 1, wherein
the aromatic nitro compounds have the formula I:

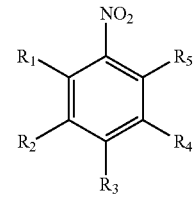

Formula I and the aniline compounds have the formula II:

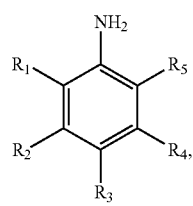

Formula II wherein $R_1$-$R_5$ are the same or different from each other and each is selected from the group consisting of a hydrogen atom, halogen atom, C1-C6 alkyl, phenyl and its substituents, benzyl and its substituents, $SR_6$, $OR_7$, $COOR_8$, $CONR_9R_{10}$ and CN; wherein $R_6$, $R_7$, $R_8$, $R_9$ and $R_{10}$ each is selected from the group consisting of a hydrogen atom, C1-C6 alkyl, phenyl and its substituents, and benzyl and its substituents.

7. The method according to claim 1, wherein the reaction is carried out in the presence of a protic solvent.

8. The method according to claim 1, wherein the hydrazine hydrate is a hydrazine hydrate aqueous solution with a mass concentration of 40-80%.

9. The method according to claim 1, further comprising filtering the reaction mixture after reaction, recovering a filter residue from the filtered reaction mixture, and adding the recovered filter residue to the reaction as a recycled catalyst.

10. The method according to claim 7, wherein the protic solvent is selected from the group consisting of water, methanol, ethyl alcohol, isopropanol, and a combination thereof.

* * * * *